US005952524A

United States Patent [19]

Eliu et al.

[11] Patent Number: 5,952,524

[45] Date of Patent: Sep. 14, 1999

[54] PROCESS

[75] Inventors: Victor Eliu, Lörrach, Germany; Werner Kanert, Hegenheim, France; Adriano Indolese, Möhlin; Ian John Fletcher, Magden, both of Switzerland; Julia Völkel, Grenzach-Wyhlen, Germany; Anita Schnyder, Allschwil, Switzerland

[73] Assignee: Ciba Specialty Chemicals Corporation, Tarrytown, N.Y.

[21] Appl. No.: 09/065,270

[22] Filed: Apr. 23, 1998

[30] Foreign Application Priority Data

Apr. 24, 1997 [GB] United Kingdom .................. 9708304

[51] Int. Cl.[6] .................................................. C07C 321/00

[52] U.S. Cl. ................................................ 562/41; 526/88

[58] Field of Search ......................................... 562/41, 88

[56] References Cited

U.S. PATENT DOCUMENTS

| | | | |
|---|---|---|---|
| 3,980,713 | 9/1976 | Matsunaga et al. | 585/26 |
| 5,231,223 | 7/1993 | Bader et al. | 562/87 |
| 5,360,924 | 11/1994 | Beller et al. | 560/55 |
| 5,516,932 | 5/1996 | Beller et al. | 560/104 |

FOREIGN PATENT DOCUMENTS

| | | |
|---|---|---|
| 0584043 | 2/1994 | European Pat. Off. . |
| 0606057 | 7/1994 | European Pat. Off. . |
| 1389996 | 5/1973 | United Kingdom . |
| 2320496 | 6/1998 | United Kingdom . |

OTHER PUBLICATIONS

J. Org. Chem., vol. 46, (1981), pp. 4885–4888.

*Primary Examiner*—Gary Geist
*Assistant Examiner*—Brian J. Davis
*Attorney, Agent, or Firm*—Kevin T. Mansfield

[57] ABSTRACT

The present invention provides a process for the production of a compound of formula:

(1)

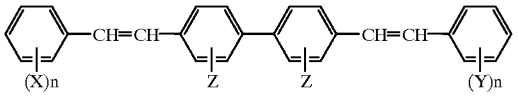

in which X and Y, independently, are hydrogen, halogen, $NO_2$, $CF_3$, CN, $C_1$–$C_4$alkyl, $C_1$–$C_4$alkoxy, COO—$C_1$–$C_4$alkyl, CO—$C_1$–$C_4$alkyl, NH—($C_1$–$C_4$alkyl), N($C_1$–$C_4$alkyl)$_2$, NH($C_1$–$C_4$alkyl-OH), N($C_1$–$C_4$alkyl-OH)$_2$, COOH or $SO_3H$ or an ester or amide thereof, or COOM or $SO_3M$ in which M is Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups;

Z is hydrogen, $C_1$–$C_4$alkyl, $C_1$–$C_4$alkoxy, $CF_3$, halogen (F, Cl, Br, I), $SO_3H$ or $SO_3M$ in which M has its previous significance; and n is 1 or 2; comprising A) reacting a diazonium compound having the formula:

(2)

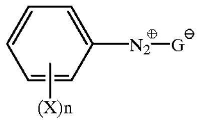

in which X and n have their previous significance and G is a counter ion, with ethylene in the presence of an inorganic or organic palladium compound, or a mixture thereof, as catalyst-precursor, to produce a compound having the formula:

(3)

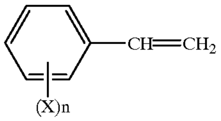

in which X and n have their previous significance; and

B) reacting 2 moles of the compound of formula (3) with 1 mole of a compound having the formula:

(4)

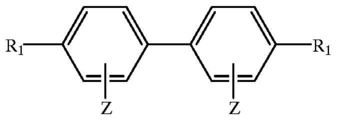

In which Z has its previous significance and each $R_1$ is the same and is a bromine or iodine atom, in the presence of an inorganic or organic palladium compound, or a mixture thereof, as catalyst-precursor, to produce a compound having the formula (1). The compounds of formula (1) are useful as fluorescent whitening agents.

25 Claims, No Drawings

PROCESS

The present invention relates to a process for the production of fluorescent whitening agents and, in particular, to a process for the production of distyryl-biphenyl fluorescent whitening agents.

The compounds of formula:

(1)

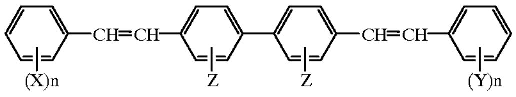

in which X and Y, independently, are hydrogen, halogen, $NO_2$, $CF_3$, CN, $C_1$–$C_4$alkyl, $C_1$–$C_4$alkoxy, COO—$C_1$–$C_4$alkyl, CO—$C_1$–$C_4$alkyl, NH—($C_1$–$C_4$alkyl), N($C_1$–$C_4$alkyl)$_2$, NH($C_1$–$C_4$alkyl-OH), N($C_1$–$C_4$alkyl-OH)$_2$, COOH or $SO_3H$ or an ester or amide thereof, or COOM or $SO_3M$ in which M is Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups;

Z is hydrogen, $C_1$–$C_4$alkyl, $C_1$–$C_4$alkoxy, $CF_3$, halogen, $SO_3H$ or $SO_3M$ in which M has its previous significance; and n is 1 or 2;

are known fluorescent whitening agents or are precursors therefor.

BACKGROUND OF INVENTION

In U.S. Pat. No. 3,980,713 there is described a method for the production of distyryl-biphenyl fluorescent whitening agents comprising reacting 1 mole of 4,4'-diiodobiphenyl with 2 mols of a styrene compound, such as a styrene sulfonic acid, in the presence of a palladium catalyst and a base at elevated temperature. The styrene sulfonic acid reactant is produced by sulfonation of styrene, which results in a mixture of 2- and 4-styrene sulfonic acid. If a sulfonated distyryl-biphenyl fluorescent whitening agent of specific structure is desired, however, this mixture must be subjected to a separation procedure, prior to reaction with 4,4'-diiodobiphenyl. Other processes which are disclosed for the production of the styrene compound reactants are the dehydration of an approriate ethylbenzene, the cleaving off of hydrogen halide from a halogenoalkylbenzene or the reaction of ethylene with a bromo- or iodobenzene in the presence of a palladium catalyst and a base.

A new route to the compounds of formula (1) has now been found which uses a simpler process for the production of the styrene reactant and which provides high yields of the end products of formula (1).

BRIEF SUMMARY OF THE INVENTION

Accordingly, the present invention provides a process for the production of a compound of formula:

(1)

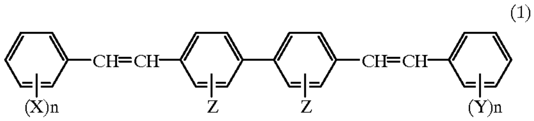

in which X and Y, independently, are hydrogen, halogen, $NO_2$, $CF_3$, CN, $C_1$–$C_4$alkyl, $C_1$–$C_4$alkoxy, COO—$C_1$–$C_4$alkyl, CO—$C_1$–$C_4$alkyl, NH—($C_1$–$C_4$alkyl), N($C_1$–$C_4$alkyl)$_2$, NH($C_1$–$C_4$alkyl-OH), N($C_1$–$C_4$alkyl-OH)$_2$, COOH or $SO_3H$ or an ester or amide thereof, or COOM or $SO_3M$ in which M is Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups;

Z is hydrogen, $C_1$–$C_4$alkyl, $C_1$–$C_4$alkoxy, $CF_3$, halogen (F, Cl, Br, I), $SO_3H$ or $SO_3M$ in which M has its previous significance; and n is 1 or 2; comprising A) reacting a diazonium compound having the formula:

(2)

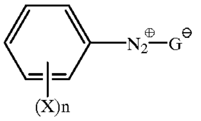

in which X and n have their previous significance and G is a counter ion, with ethylene in the presence of an inorganic or organic palladium compound, or a mixture thereof, as catalyst-precursor, to produce a compound having the formula:

(3)

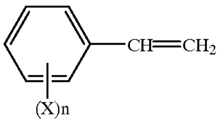

in which X and n have their previous significance; and

B) reacting 2 moles of the compound of formula (3) with 1 mole of a compound having the formula:

(4)

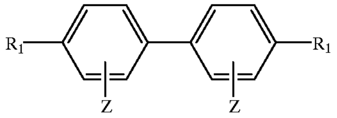

in which Z has its previous significance and each $R_1$ is the same and is a bromine or iodine atom, in the presence of an inorganic or organic palladium compound, or a mixture thereof, as catalyst-precursor, to produce a compound having the formula (1).

It is advantageous to conduct step B) of the process without the intermediate isolation of the reactant of formula (3) obtained in step A).

If, in the compound of formula (4), $R_1$ is an iodine atom, the iodine released during step B) may be recovered by separating the waste water from the reaction mixture of step B), and treating it with the equivalent amount of chlorine. The iodine separates out in crystalline form and, after separation by filtration, may be recycled into the process. If, in the compound of formula (4), $R_1$ is a bromine atom, the bromine released during step B) may be recovered by separating the waste water from the reaction mixture of step B), and treating it with the equivalent amount of chlorine, with stirring under reflux conditions. The bromine is separated by distillation and may then be separated from water and recycled into the process.

In the compounds of formula (1), preferably X and Y, independently, are hydrogen, cyano, COOM or $SO_3M$ in which M has its previous significance, and preferably Z is hydrogen and n is 1. If the substituents X or Y are negatively charged, then the resulting diazonium salt of formula (2) may be present as an internal salt.

In the compounds of formula (2), preferably G is $H_2PO_4^-$, $HPO_4^{2-}$, $NO_3^-$, $CF_3COO^-$, $^-OOC$—$COO^-$ (oxalate), $Cl_3CCOO^-$, $ClCH_2COO^-$, $I^-$, $Cl^-$, $Br^-$, $F^-$, $ClO_4^-$, $PF_6^-$, $BF_4^-$, $Oac^-$, $HSO_4^-$, $SO_4^{2-}$, $CH_3(C_6H_4)SO_3^-$ or $CH_3SO_3^-$, especially $H_2PO_4^-$, $Cl_3CCOO^-$, $ClCH_2COO^-$, $PF_6^-$, $BF_4^-$, $Oac^-$, $HSO_4^-$, $SO_4^{2-}$, $CH_3(C_6H_4)SO_3^-$ or $CH_3SO_3^-$.

The diazonium compounds having the formula (2) are known compounds and may be produced by methods known per se. The diazonium compounds may be formed in situ or added as a salt of formula (2). The in situ formation may also be conducted in the presence of the olefins of formula $CHR_2$=$CHR_3$ in which $R_2$ is H, F, Cl, Br or —$COOR_4$ (in which $R_4$ is H or $C_1$–$C_4$alkyl) and $R_3$ is —COO($C_1$–$C_4$alkyl), —$COR_4$ or $C_1$–$C_2$alkyl optionally substituted by halogen, e.g. by the addition of alkyl nitrites such as t-butyl nitrite, as described in J. Org. Chem. vol.46, pp. 4885–4888 (1981).

For example, the said diazonium compounds may be produced by reacting the corresponding amines with an alkali metal nitrite, an alkyl nitrite or nitrosylsulfonic acid, optionally in the presence of an acid, in aqueous or in organic solution. If the diazotisation is conducted in organic solution, it is preferred that the water, produced as a by-product of the diazotisation reaction, is removed either as it is formed, or prior to the reaction step B). The removal of such water may be conveniently conducted by effecting the diazotisation in the presence of water-binding materials such as acetic anhydride, sodium sulfate, calcium chloride or molecular sieves.

When n is 1, examples of the amino component precursors of the diazo salt starting materials of formula (2) include, e.g., aniline, 2-, 3- or 4-chloro-aniline, 2-, 3- or 4-bromo-aniline, 2-, 3- or 4-iodo-aniline, 2-, 3- or 4-trifluoromethyl-aniline, 2-, 3- or 4-nitrilo-aniline, 2-, 3- or 4-methyl-aniline, 2-, 3- or 4-ethyl-aniline, 2-, 3- or 4-n-propyl-aniline, 2-, 3- or 4-n-butyl-aniline, 2-, 3- or 4-methoxy-aniline, 2-, 3- or 4-ethoxy-aniline, 2-, 3- or 4-n-propoxy-aniline, 2-, 3- or 4-n-butoxy-aniline, 2-, 3- or 4-amino-benzoic acid or its methyl, -ethyl-, n-propyl or n-butyl ester, 2-, 3- or 4-amino-acetophenone, 2-, 3- or 4-methylamino-aniline, 2-, 3- or 4-ethylamino-aniline, 2-, 3- or 4-hydroxyethyleneamino-aniline, 2-, 3- or 4-di(hydroxyethyleneamino)-aniline and 2-, 3- or 4-aminobenzene sulfonic acid. In the cases of 2-, 3- or 4-aminobenzoic acid and 2-, 3- or 4-aminobenzene sulfonic acid, these acids may be used in the form of their respective salts in which the cation M has its previous significance and is preferably sodium.

When n is 2, examples of the amino component precursors of the diazo salt starting materials of formula (2) include, e.g., 3- or 4-aminobenzo-1,2-dinitrile, 3- or 4-aminobenzene-1,2-dicarboxylic acid or its dimethyl, -diethyl-, di-n-propyl or di-n-butyl ester, aminobenzene-2,4-disulfonic acid, aminobenzene-3,5-disulfonic acid or aminobenzene-2,5-disulfonic acid. In the cases of 3- or 4-aminobenzene-1,2-dicarboxylic acid and aminobenzene-2,4-disulfonic acid, aminobenzene-3,5-disulfonic acid or aminobenzene-2,5-disulfonic acid, these acids may be used in the form of their respective salts in which the cation M has its previous significance and is preferably sodium.

The preferred amino component precursor of the diazonium compound of formula (2) is 2-, 3- or 4-aminobenzene sulfonic acid.

The reactants of formula (4) are known compounds and may be produced by known methods, for example by the bromination or iodination of biphenyl.

DETAILED DESCRIPTION OF THE INVENTION

The preferred product of the process of the present invention has the formula:

(101)

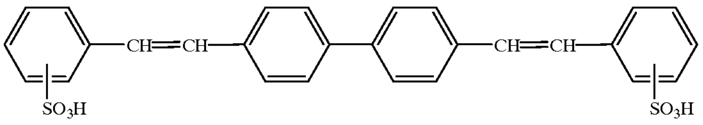

or an alkali metal salt, especially the sodium salt thereof.

The palladium catalyst precursor used in step A) and B) may be generated, in situ or ex situ, by reduction of a palladium (II) compound, optionally in the presence of a salt such as sodium acetate, and optionally in the presence of suitable ligand-forming or colloid-stabilising compounds. Suitable palladium (II) compounds include $PdCl_2$, $PdBr_2$, $Pd(NO_3)_2$, $H_2PdCl_4$, $Pd(OOCCH_3)_2$, $[PdCl_4]Na_2$, $[PdCl_4]Li_2$, $[PdCl_4]K_2$, palladium(II)acetylacetonate, dichloro-(1,5-cyclooctadiene)palladium(II), dichlorobis-(acetonitrile) palladium(II), dichlorobis-(benzonitrile)palladium(II), π-allylpalladium(II)chloride dimer, bis-(π-methallyl palladium(II)chloride) and π-allylpalladium(II) acetylacetonate. Suitable ligand-forming compounds are, for example, olefins having the formula $CHR_2$=$CHR_3$ in which $R_2$ is H, F, Cl, Br or —$COOR_4$ (in which $R_4$ is H or $C_1$–$C_4$alkyl) and $R_3$ is —COO($C_1$–$C_4$alkyl), —$COR_4$ or $C_1$–$C_2$alkyl optionally substituted by halogen; dibenzylideneacetone (dba) optionally substituted with halogen (F, Cl or Br), $SO_3M$ (in which M has its previous significance), $C_1$–$C_4$alkyl or $C_1$–$C_4$alkoxy in the benzene rings; phosphites such as those of formula $P(OR_5)$ in which $R_5$ is e.g. phenyl, $C_1$–$C_6$alkyl or a partially or perfluorinated $C_1$–$C_6$alkyl; or CO. The substituents in the benzene rings are preferably linked in the para-positions of the benzene rings. Further examples of suitable ligand-forming compounds are phosphines having the formula $PR_6R_7R_8$ or $R_6R_7P$—Q—$PR_6R_7$, whereby $R_6$, $R_7$ and $R_8$ independently represent alkyl, cycloalkyl or aryl, which may be substituted by halogen, hydroxy, alkoxy, sulphonate or carboxy groups and Q represents linear or branched, substituted or unsubstituted $C_2$–$C_{12}$alkylene, 1,2- or 1,3-$C_4$–$C_8$cycloalkylene, 1,2- or 1,3-heterocycloalkylene with 5 or 6 ring members and O or N as the heteroatom or ferrocenyl. The residues $R_6$, $R_7$ and $R_8$ are preferably identical and may be linear or branched containing 1–12, more preferably 1–8 and, especially preferred, 1–6 carbon atoms. Examples of alkyl groups are methyl, ethyl, n- and i-propyl, n-, i-, and t-butyl, the isomers of pentyl, hexyl, heptyl, octyl, nonyl, decyl, undecyl, dodecyl, tridecyl, tetradecyl, pentadecyl, hexadecyl, heptadecyl, octadecyl and eicosyl, preferred examples being methyl, ethyl, n- and i-propyl, n-, i-, and t-butyl, 1-, 2- or 3-pentyl and 1-, 2-, 3-, or 4-hexyl. Where $R_6$, $R_7$ and $R_8$ represent cycloalkyl, these are preferably $C_5$–$C_8$cycloalkyl, especially $C_5$- or $C_6$cycloalkyl, as exemplified by cyclobutyl, cycloheptyl, cyclooctyl or, especially, cydopentyl and cyclohexyl. Where $R_6$, $R_7$ and $R_8$ represent aryl, these are preferably $C_6$–$C_{12}$-aryl, especially preferred being phenyl, biphenyl or naphthyl. Where Q represents linear or branched alkylene this is preferably 1,2- or 1,3-alkylene with preferably 2 to 6 carbon atoms such as ethylene, 1,2-propylene or 1,2-butylene. Examples of Q as cycloalkylene are 1,2- and 1,3-cyclopentylene and 1,2- or 1,3-cyclohexylene, whilst those of heterocycloalkylene are 1,2- and 1,3-pyrrolidine, 1,2- and 1,3-piperidine and 1,2- and 1,3-tetrahydrofuran. Q may also represent substituted or unsubstituted 1,1'-ferrocene. Especially preferred examples of phosphine ligands are $(C_6H_5)_3P$, (2-methyl-$C_6H_4)_3P$, (3-methyl-$C_6H_4)_3P$, (4-methyl-$C_6H_4)_3P$, (2,4-dimethyl-$C_6H_3)_3P$, (2,6-dimethyl-$C_6H_3)_3P$, (4-methoxy-$C_6H_4)_3P$, $(C_4H_9)_3P$, $(C_6H_{11})_3P$, 1,2-bis(diphenyl)phosphino-ethane, 1,3-bis(diphenyl)phosphinopropane, 1,4-bis(diphenyl) phosphinobutane or 1,1'-bis(diphenyl)phosphinoferrocene.

The ligand-forming compounds may be used alone or in combinations of at least two compounds. The production of the palladium catalyst precursor used in step A) and B) are described in more detail in EP-584,043.

Suitable reducing agents are, e.g., CO, $H_2$, formates, primary or secondary $C_1$–$C_8$alkanols, hydrazine, amines, mixtures of CO with alkanols or water, or the ligating olefine per se.

The catalyst may be added as $Pd(dba)_2$, $Pd(dba)_3$.solvent $Pd_2(dba)_3$ or $Pd_2(dba)_3$.solvent. The dba ligand may be optionally substituted in the aromatic part as described above. Optionally, the catalyst may be added as Pd on a suitable support such as charcoal or $Al_2O_3$ (EP-606,058).

Preferably the palladium catalyst is used in an amount of 0.0001 to 5 mole %, based on the diazonium salt of formula (2) or the styrene compound of formula (3).

After completion of the process according to the present invention, the palladium catalyst is preferably recovered for re-use, by methods which are well-known.

The process according to the present invention may be effected in water, as solvent, in which case, preferably the palladium compound catalyst used contains one or more water-solubilising groups such as sulfo groups or carboxyl groups.

If desired, the process according to the present invention may be conducted in a-two-phase solvent system comprising water and a water-insoluble organic solvent, such as halogenated hydrocarbon, e.g. dichloromethane, or a $C_5$–$C_{12}$alcohol such as n-pentanol. In such two-phase reaction systems, optionally a phase transfer catalyst or a suitable surfactant may be present.

Preferably, however, the process according to the present invention is conducted in an organic solvent, preferably in one or more of the following: alcohols; ketones; carboxylic acids; sulfones; sulfoxides; N,N-tetrasubstituted ureas; N-alkylated lactams or N-dialkylated acid amides; ethers; aliphatic, cycloaliphatic or aromatic hydrocarbons, which may be optionally substituted with F, Cl or $C_1$–$C_4$alkyl; carboxylic acid esters and lactones; nitriles; and glymes.

Some specific examples of solvents are:

alcohols: methanol, ethanol, propanol, isopropanol, butanol, t-butanol, hexanol, heptanol, octanol, ethylene glycol and di-, tri- and tetra-ethylene glycol;

ketones: acetone, methylethylketone, methylisobutylketone and cyclohexanone;

carboxylic acids: ethanoic acid, propanoic acid and chloroacetic acid;

sulfones: dimethylsulfone, diethylsulfone, tetramethylenesulfone and sulfolan;

sulfoxides: dimethylsulfoxide;

N,N-tetrasubstituted ureas: N-methylethyl-N'-methylethylurea, N-dimethyl-N'-dipropylurea, tetramethylurea, tetraethylurea, N,N'-dimethyl-N,N'-1,3-propyleneurea, N,N'-dimethyl-N,N'-ethyleneurea;

N-alkylated lactams: N-methylpyrrolidone and N-ethylpyrrolidone;

N-dialkylated acid amides: N-dimethylformamide, N-diethylformamide and N-dimethylacetamide;

ethers: polyethylglycolether, di-, tri- and tetra-ethyleneglycoldimethylether, di-, tri- and tetra-ethyleneglycoldiethylether, terahydrofuran, dioxan, methyl-t-butylether, diethyleneglycolmonomethylether and ethyleneglycolmonomethylether;

aliphatic hydrocarbons: methylene chloride, pentane and hexane;

cycloaliphatic hydrocarbons: cyclohexane and decahydronaphthalene;

aromatic hydrocarbons: xylene, terahydronaphthalene and dichlorobenzene;

carboxylic acid esters: methyl benzoate, ethylacetate, γ-butyrolactone and n-butylacetate;

nitriles: acetonitrile, benzonitrile and phenylacetonitrile;

glymes: di-, tri- and tetra-glymes.

The process of the present invention is preferably conducted in the presence of a base which may be an organic base, an inorganic base or a mixture thereof and which is added prior to step B). The base is also used as a buffer to neutralise mineral acid present during the formation of the diazonium salt reactants. The base may be used in at least equimolar amounts relative to the diazonium salt of formula (2) or (3) and preferably in an excess of up to 10 moles. Examples of suitable bases are Li-, Na-, K-, $NH_4$-, Mg-, Ca- and $NH(C_1$–$C_{18}alkyl)_3$-salts of carboxylic acids such as $C_1$–$C_4$carboxylic acids or benzoic acid. Specific examples of suitable bases are lithium-, potassium- or sodium acetate, -butyrate, -propionate and -stearate; barium- and calcium acetate; calcium propionate and -stearate; lithium- and sodium benzoate; ammonium acetate; and salts of acetic acid with triethylamine, tri-n-butylamine, tri-(2-ethylhexylamine), tri-n-octylamine and tri-n-dodecylamine. Preferred are alkaline metal acetates which form acetic acid as a desirable component in the arylation step B). Particularly preferred bases are sodium and potassium acetate, and sodium and potassium bicarbonate, used in excess. The bases may also be used as salts in the catalyst generation, as described above.

The process of the present invention is preferably conducted at a temperature in the range of from −10 to 160° C., more preferably at a temperature in the range of from −10 to 150° C.

The following Examples further illustrate the present invention. Parts and percentages shown therein are by weight unless otherwise stated.

EXAMPLE 1

(101)

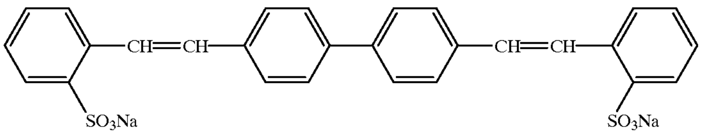

A) Preparation of 4,4'-diiododiphenyl 15.4 g of diphenyl are added to a reaction vessel containing 170 ml of acetic acid and 30 ml of water. At 20° C., with good stirring, there are added, successively, 34 g of potassium persulfate, 26 g of crystalline iodine (purity above 97%) and 12.6 g of conc. sulfuric acid (purity above 98%). The reaction mixture is heated slowly to reflux temperature and held at this temperature for 6 hours, during which time the dark colour of the reaction mixture continuously lightens. Finally, the reaction mixture is present as a colourless suspension. The amount of diiododiphenyl obtained is 39.6 g (>98% of the 4,4'-isomer). The suspension is filtered with suction.

B) Preparation of the diazonium salt of 2-aminobenzenesulfonic acid

Into 150 g of anhydrous acetic acid, there are stirred 42 g of technical grade 2-aminobenzenesulfonic acid (38 g of 100% pure 2-aminobenzenesulfonic acid) and 3.8 g of conc. sulfuric acid (purity 96%), while keeping the reaction mixture at 15–20° C., by applying external cooling. At the same temperature, over 90 minutes, there are added 30.4 g of a 50% sodium nitrite solution. The reaction mixture is stirred for a further hour while the temperature is kept below 20° C. by cooling. Finally, the nitrite excess is determined and the necessary amount of 2-aminobenzene sulfonic acid is added to remove the excess.

C) Preparation of 2-styrenesulfonic acid 80 g of acetic anhydride are added, dropwise, over 3 hours to the reaction mixture obtained in part B). A weak exothermic reaction takes place. The reaction mixture is stirred for 1 hour, 36 g of anhydrous sodium acetate are added, the reaction mixture is stirred well until it becomes homogeneous and it is then transferred into a high pressure reactor. The reaction mixture is treated with 0.6 g of palladium[bis(dibenzalacetone)]$_2$ and, after 5 minutes, the reactor is filled with an inert atmosphere of nitrogen. The pressure in the reactor is then increased to 50 bars by introducing ethylene and the reaction is conducted at 18–25° C. over 10 hours. The pressure of the mixture of ethylene and nitrogen is then reduced. There is obtained a whitish-grey suspension of the sodium salt of 2-styrenesulfonic acid in acetic acid. The evaluation of the degree of conversion of the diazo reactant is effected with an alkaline H-acid solution, for full conversion, no further violet coloured ring can be observed. The resulting suspension contains 43 g of the sodium salt of 2-styrenesulfonic acid and is used for the subsequent reaction step.

D) Reaction of 2-styrenesulfonic acid with 4,4'-diiododiphenyl

The 4,4'-diiododiphenyl, moist with acetic acid, from step A) is mixed with the suspension of 2-styrenesulfonic acid from step C) and the mixture is treated with 32.4 g of anhydrous sodium bicarbonate, with stirring and cooling. 0.6 g of palladium[bis(dibenzalacetone)]$_2$ is added and the mixture is heated to 110° C. and stirred for 25 hours. Gas is released from the reaction mixture, strongly at first, later ever more weakly until finally gas release ceases completely.

The acetic acid is distilled off under vacuum. The dry substance so obtained is made up to 300 ml with water, heated to 90° C., treated with 3 g of active charcoal and the insoluble components are separated by filtration. Crystallisation of the reaction product from the filtered solution is induced by cooling the solution to 15° C. using a ramp. Finally, the product which crystallises out is separated by filtration, washed and dried. In this way, 50 g of the compound of formula (101) are obtained, representing a yield of 89% by weight, based on the weight of the diphenyl starting material.

The iodine is recovered by treating the separated waste water with the equivalent amount of chlorine at 20° C., with stirring. The iodine separates out in crystalline form, is separated by filtration and returned to step A).

EXAMPLE 2

(101)

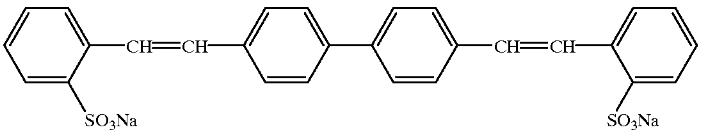

Steps A) and B) are carried out as described in Example 1.

C) Preparation of 2-styrenesulfonic acid 80 g of acetic anhydride are added, dropwise, over 3 hours to the reaction mixture obtained in part B). A weak exothermic reaction takes place. The reaction mixture is stirred for 1 hour, 36 g of anhydrous sodium acetate are added, the reaction mixture is stirred well until it becomes homogeneous and it is then transferred into a high pressure reactor. The reaction mixture is treated with 0.6 g of palladium[bis(dibenzalacetone)]$_2$ and, after 5 minutes, the reactor is filled with an inert atmosphere of nitrogen. The pressure in the reactor is then increased to 50 bars by introducing ethylene and the reaction is conducted at 18–25° C. over 10 hours.

The pressure of the mixture of ethylene and nitrogen is then reduced. There is obtained a whitish-grey suspension of the sodium salt of 2-styrenesulfonic acid in acetic acid. The evaluation of the degree of conversion of the diazo reactant is effected with an alkaline H-acid solution, for full conversion, no further violet coloured ring can be observed. The resulting suspension contains 43 g of the sodium salt of 2-styrenesulfonic acid and is filtered and used for the subsequent reaction step.

D) Reaction of 2-styrenesulfonic acid with 4,4'-diiododiphenyl

The 4,4'-diiododiphenyl, moist with acetic acid, from step A) is mixed with the moist 2-styrenesulfonic acid from step C) in 300 ml of water and the mixture is treated with 32.4 g of anhydrous sodium bicarbonate, with stirring and cooling. The mixture is then heated to 98° C. and stirred for 25 hours. Gas is released from the reaction mixture, strongly at first, later ever more weakly until finally gas release ceases completely.

The reaction mixture is cooled to 90° C., treated with 3 g of active charcoal and the insoluble components are separated by filtration. Crystallisation of the reaction product from the filtered solution is induced by cooling the solution to 15° C. using a ramp. Finally, the product which crystallises out is separated by filtration, washed and dried. In this way, 50 g of the compound of formula (101) are obtained, representing a yield of 89% by weight, based on the weight of the diphenyl starting material.

The iodine is recovered by treating the separated waste water with the equivalent amount of chlorine at 20° C., with stirring. The iodine separates out in crystalline form, is separated by filtration and returned to step A).

EXAMPLE 3

(102)

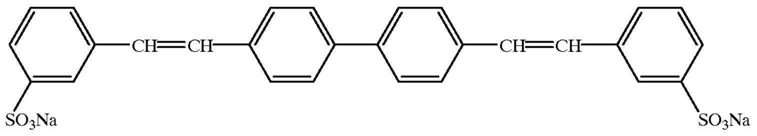

A) Preparation of 4,4'-dibromodiphenyl 15.4 g of diphenyl are added to a reaction vessel containing 170 ml of acetic acid and 30 ml of water. At 20° C., with good stirring, there are added, successively, 34 g of potassium persulfate, 17 g of bromine and 12.6 g of conc. sulfuric acid (purity above 98%). The reaction mixture is heated slowly to reflux temperature and held at this temperature for 2 hours, during which time the dark colour of the reaction mixture continuously lightens. Finally, the reaction mixture is present as a colourless suspension. The amount of dibromodiphenyl obtained is 31 g (>98% of the 4,4'-isomer). The suspension is filtered with suction, washed and dried.

B) Preparation of the diazonium salt of 3-aminobenzenesulfonic acid

Into 100 g of water, there are stirred 43.3 g of 100% pure 3-aminobenzenesulfonic acid and 13.2 g of conc. sulfuric acid (purity 96%), while keeping the reaction mixture at 15–20° C., by applying external cooling. At the same temperature, over 60 minutes, there are added 34.5 g of a 50% sodium nitrite solution. The reaction mixture is stirred for a further 30 minutes while the temperature is kept below 20° C. by cooling. Finally, the nitrite excess is determined and the necessary amount of 3-aminobenzene sulfonic acid is added to remove the excess. The suspension is filtered with suction, washed with ice water and well stripped to obtain 50 g of an almost white filtercake.

C) Preparation of 3-styrenesulfonic acid 30.6 g of acetic anhydride are added, dropwise, over 3 hours to the moist diazo presscake obtained in step B) in 200 ml of pentanol. A weak exothermic reaction takes place. The reaction mixture is stirred for 1 hour, 20.6 g of anhydrous sodium acetate are added, the reaction mixture is stirred well until it forms a suspension and it is then transferred into a high pressure reactor. The reaction mixture is treated with 0.6 g of palladium[bis(dibenzalacetone)]$_2$ and, after 5 minutes, the reactor is filled with an inert atmosphere of nitrogen. The pressure in the reactor is then increased to 50 bars by introducing ethylene and the reaction is conducted at 18–25° C. over 10 hours. The pressure of the mixture of ethylene and nitrogen is then reduced. There is obtained a whitish-grey suspension of the sodium salt of 3-styrenesulfonic acid in pentanol/acetic acid. The evaluation of the degree of conversion of the diazo reactant is effected with an alkaline H-acid solution, for full conversion, no further violet coloured ring can be observed. The resulting suspension is filtered with suction, washed and dried and is used as such for the next reaction step. The dried intermediate has a weight of 63.4 g and contains 60–70% of the sodium salt of 2-styrenesulfonic acid and 30% of sodium acetate.

D) Reaction of 3-styrenesulfonic acid with 4,4'-dibromodiphenyl 30 g of 4,4'-dibromodiphenyl from step A) is stirred into 240 g of dimethylformamide and then 65 g of 3-styrenesulfonic acid from step D) are added. To the resulting suspension there are added 34 g of sodium bicarbonate and 0.45 g of palladium[bis(dibenzalacetone)]$_2$ and the mixture is heated to 120° C. Gas is released from the reaction mixture, strongly at first, later ever more weakly until finally gas release ceases completely. After being allowed to stand for 20 hours, the reaction mixture is worked up.

The reaction mass is heated to reflux in a mixture of 250 g of dimethylacetamide and 500 g of water, treated with 2 g of active charcoal and the insoluble components are separated by filtration. Crystallisation of the reaction product from the filtered solution is induced by cooling the solution to 15° C. using a ramp. Finally, the product which crystallises out is separated by filtration, washed and dried. In this way, 32.5 g of the compound of formula (102) are obtained, representing a yield of 83% by weight, based on the weight of the diphenyl starting material.

The bromine is recovered by treating the separated waste water with the equivalent amount of chlorine at the reflux temperature, with stirring. The bromine separates out by distillation, is separated from the water and returned to step A).

EXAMPLE 4

(102)

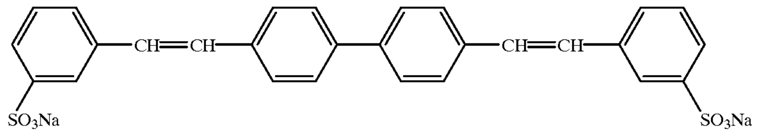

A) Preparation of 4,4'-dibromodiphenyl 10.4 g of diphenyl are added to a reaction vessel containing 120 ml of acetic acid and 20 ml of water. At 20° C., with good stirring, there are added, successively, 23 g of potassium persulfate, 11,5 g of bromine and 18.6 g of conc. sulfuric acid (purity above 98%). The reaction mixture is heated slowly to reflux temperature and held at this temperature for 2 hours, during which time the dark colour of the reaction mixture continuously lightens. Finally, the reaction mixture is present as a colourless suspension. The amount of dibromodiphenyl obtained is 21 g (>98% of the 4,4'-isomer). The suspension is filtered with suction, washed and dried.

B) Preparation of the diazonium salt of 3-aminobenzenesulfonic acid

Into 133.2 g of water, there are stirred 69.2 g of 100% pure 3-aminobenzenesulfonic acid and 22 g of conc. sulfuric acid (purity 96%), while keeping the reaction mixture at 15–20° C., by applying external cooling. At the same temperature, over 90 minutes, there are added 27.6 g of sodium nitrite in 93.2 g of water. The reaction mixture is stirred for a further 60 minutes while the temperature is kept at 15° C. by cooling. Finally, the nitrite excess is determined and the necessary-amount of 3-aminobenzene sulfonic acid is added to remove the excess. The suspension is filtered with suction, washed with 200 g of ice water and 300 g of n-pentanol to yield a moist diazo presscake.

C) Preparation of 3-styrenesulfonic acid

The moist diazo presscake obtained in step B) was suspended in 350 g of n-pentanol and cooled to 10° C. 40.8 g of acetic anhydride and 32.8 g of anhydrous sodium acetate are added, dropwise, over 1 hour. A weak exothermic reaction takes place. The reaction mixture is stirred for 1 hour at 10° C. and then transferred to a high pressure reactor. The reaction mixture is treated with 0.636 g of palladium chloride solution in hydrochloric acid (commercially available with 20% palladium content) and, after 5 minutes, the reactor is filled with an inert atmosphere of nitrogen. The pressure in the reactor is then increased to 50 bars by introducing ethylene (60 g) at a temperature below 16° C. and the reaction is conducted at 25° C. for 15 hours. The pressure of the mixture of ethylene and nitrogen is then reduced. There is obtained a whitish-grey suspension of the sodium salt of 3-styrenesulfonic acid in pentanol/acetic acid. The evaluation of the degree of conversion of the diazo reactant is effected with an alkaline H-acid solution, for full conversion, no further violet colouration can be observed. The resulting suspension is filtered with suction. The moist presscake contains 60–70% of the sodium salt of 3-styrenesulfonic acid and 10% of the 3-stilbene sulfonic acid and sodium acetate.

D) Reaction of 3-styrenesulfonic acid with 4,4'-dibromodiphenyl 21 g of 4,4'-dibromodiphenyl from step A), 66.6 g (ca 0.2 M as determined by HPLC) of the moist 3-styrene sulfonic acid from step C), 21.2 g of anhydrous sodium carbonate, 0.493 g of hydroquinone monomethyl ether and 0.349 g of triphenylphosphine are added to a vessel which is then filled with an inert atmosphere of nitrogen. 300 ml of de-aerated dimethylacetamide are then added and the mixture heated to 155° C. Carbon dioxide is released from the reaction mixture, strongly at first, later ever more weakly until finally gas release ceases completely. The reaction mixture is stirred overnight at this temperature and, after being allowed to cool, filtered with suction. The moist residue (214.9 g) yields 27.9 g of the compound of formula (102).

The bromine is recovered by treating the separated waste water with the equivalent amount of chlorine at the reflux temperature, with stirring. The bromine separates out by distillation, is separated from the water and returned to step A).

We claim:

1. A process for the production of a compound of formula:

(1)

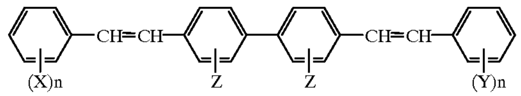

in which X and Y, independently, are hydrogen, halogen, $NO_2$, $CF_3$, CN, $C_1$–$C_4$alkyl, $C_1$–$C_4$alkoxy, COO—$C_1$–$C_4$alkyl, CO—$C_1$–$C_4$alkyl, NH—($C_1$–$C_4$alkyl), N($C_1$–$C_4$alkyl)$_2$, NH($C_1$–$C_4$alkyl-OH), N($C_1$–$C_4$alkyl-OH)$_2$, COOH or $SO_3H$ or an ester or amide thereof, or COOM or $SO_3M$ in which M is Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups;

Z is hydrogen, $C_1$–$C_4$alkyl, $C_1$–$C_4$alkoxy, $CF_3$, halogen (F, Cl, Br, I), $SO_3H$ or $SO_3M$ in which M has its previous significance; and n is 1 or 2; comprising A) reacting a diazonium compound having the formula:

(2)

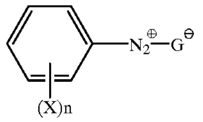

in which X and n have their previous significance and G is a counter ion, with ethylene in the presence of an inorganic or organic palladium compound, or a mixture thereof, as catalyst-precursor, to produce a compound having the formula:

(3)

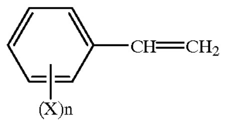

in which X and n have their previous significance; and

B) reacting 2 moles of the compound of formula (3) with 1 mole of a compound having the formula:

(4)

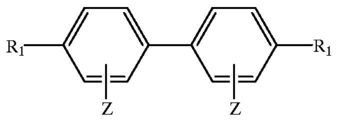

In which Z has its previous significance and each $R_1$ is the same and is a bromine or iodine atom, in the presence of an inorganic or organic palladium compound, or a mixture thereof, as catalyst-precursor, to produce a compound having the formula (1), in which step B) of the process is conducted without the intermediate isolation of the reactant of formula (3) obtained in step A).

2. A process as claimed in claim 1 in which in the compounds of formula (1), X and Y, independently, are hydrogen, cyano, COOM or $SO_3M$ in which M is as defined in claim 1, Z is hydrogen and n is 1.

3. A process according to claim 1 in which in the compounds of formula (2), G is $H_2PO_4^-$, $HPO_4^{2-}$, $NO_3^-$, $CF_3COO^-$, $OOC—COO^-$ (oxalate), $Cl_3CCOO^-$, $ClCH_2COO^-$, $I^-$, $Cl^-$, $Br^-$, $F^-$, $ClO_4^-$, $PF_6^-$, $BF_4^-$, $Oac^-$, $HSO_4^-$, $SO_4^{2-}$, $CH_3(C_6H_4)SO_3^-$ or $CH_3SO_3^-$.

4. A process according to claim 3 in which G is $H_2PO_4^-$, $Cl_3CCOO^-$, $ClCH_2COO^-$, $PF_6^-$, $BF_4^-$, $Oac^-$, $HSO_4^-$, $SO_4^{2-}$, $CH_3(C_6H_4)SO_3^-$ or $CH_3SO_3^-$.

5. A process according to claim 1 in which n is 1 and the amino component precursor of the diazo salt starting material of formula (2) is aniline, 2-, 3- or 4-chloro-aniline, 2-, 3- or 4-bromo-aniline, 2-, 3- or 4-iodo-aniline, 2-, 3- or 4-trifluoromethyl-aniline, 2-, 3- or 4-nitrilo-aniline, 2-, 3- or 4-methyl-aniline, 2-, 3- or 4-ethyl-aniline, 2-, 3-, or 4-n-propyl-aniline, 2-, 3- or 4-n-butyl-aniline, 2-, 3- or 4-methoxy-aniline, 2-, 3- or 4-ethoxy-aniline, 2-, 3- or 4-n-propoxy-aniline, 2-, 3- or 4-n-butoxy-aniline, 2-, 3- or 4-amino-benzoic acid or its methyl, -ethyl-, n-propyl or n-butyl ester, 2-, 3- or 4-amino-acetophenone, 2-, 3- or 4-methylamino-aniline, 2-, 3- or 4-ethylamino-aniline, 2-, 3- or 4-hydroxyethyleneamino-aniline, 2-, 3- or 4-di (hydroxyethyleneamino)-aniline or 2-, 3- or 4-aminobenzene sulfonic acid.

6. A process according to claim 5 in which the amino component precursor of the diazo salt starting material of formula (2) is 2-, 3- or 4-aminobenzoic acid or 2-, 3- or 4-aminobenzene sulfonic acid, and these acids are used in the form of their respective salts in which the cation M is Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups.

7. A process according to claim 1 in which n is 2 and the amino component precursor of the diazo salt starting material of formula (2) is 3- or 4-aminobenzo-1,2-dinitrile, 3- or 4-aminobenzene-1,2-dicarboxylic acid or its dimethyl, -diethyl-, di-n-propyl or di-n-butyl ester, aminobenzene-2,4-disulfonic acid, aminobenzene-3,5-disulfonic acid or aminobenzene-2,5-disulfonic acid.

8. A process according to claim 1 in which the product of the process has the formula:

(101)

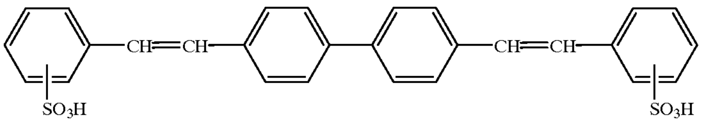

or an alkali metal salt thereof.

9. A process according to claim 5 in which the palladium catalyst precursor used in step A) and B) is generated, in situ or ex situ, by reduction of a palladium (II) compound, optionally in the presence of a salt, and optionally in the presence of a suitable ligand-forming or colloid-stabilising compound.

10. A process according to claim 9 which the palladium (II) compound is $PdCl_2$, $PdBr_2$, $Pd(NO_3)_2$, $H_2PdCl_4$, $Pd(OOCCH_3)_2$, $[PdCl_4]Na_2$, $[PdCl_4]Li_2$, $[PdCl_4]K_2$, palladium(II)acetylacetonate, dichloro-(1,5-cyclooctadiene) palladium(II), dichlorobis-(acetonitrile)palladium(II), dichlorobis-(benzonitrile)palladium(II), π-allylpalladium (II)chloride dimer, bis-(π-methallyl palladium(II)chloride) or -allylpalladium(II)acetylacetonate.

11. A process according to claim 9 in which the salt is sodium acetate.

12. A process according to claim 9 in which the ligand-forming compound is an olefin having the formula $CHR_2═CHR_3$ in which $R_2$ is H, F, Cl, Br or —$COOR_4$, and $R_3$ is —$COO(C_1$–$C_4$alkyl), —$COR_4$ or $C_1$–$C_2$alkyl optionally substituted by halogen; dibenzylideneacetone optionally substituted in the benzene rings with F, Cl or Br, $SO_3M$ in which M is Na, K, Ca, Mg, ammonium, mono-, di-, tri- or tetra-$C_1$–$C_4$alkylammonium, mono-, di- or tri-hydroxyalkylammonium or ammonium that is di- or tri-substituted with a mixture of $C_1$–$C_4$alkyl and $C_1$–$C_4$hydroxyalkyl groups, $C_1$–$C_4$alkyl or $C_1$–$C_4$alkoxy; a phosphite of the formula $P(OR_5)$ in which $R_5$ is phenyl, $C_1$–$C_6$alkyl or a partially or perfluorinated $C_1$–$C_6$alkyl; or CO.

13. A process according to claim 9 in which the ligand-forming compounds are phosphines having the formula $PR_6R_7R_8$ or $R_6R_7P—Q—P R_6R_7$, whereby $R_8$, $R_7$ and $R_8$ independently represent alkyl, cycloalkyl or aryl, which may be substituted by halogen, hydroxy, alkoxy, sulphonate or carboxy groups and Q represents linear or branched, substituted or unsubstituted $C_2$–$C_{12}$alkylene, 1,2- or 1,3-$C_4$–$C_8$cycloalkylene, 1,2- or 1,3-heterocycloalkylene with 5 or 6 ring members and O or N as the heteroatom or ferrocenyl.

14. A process according to claim 9 in which the reduction is effected using, as a reducing agent, CO, $H_2$, a formate, a primary or secondary $C_1$–$C_8$alkanol, hydrazine, an amine, a mixture of CO with an alkanol or water, or the ligating olefin per se.

15. A process according to claim 12 in which the catalyst is added as $Pd(dba)_2$, $Pd(dba)_3$.solvent $Pd_2(dba)_3$ or $Pd_2(dba)_3$.solvent.

16. A process according to claim 10 in which the palladium catalyst is used in an amount of 0.01 to 5 mole %, based on the diazonium salt of formula (2) or the styrene compound of formula (3).

17. A process according to claim 1 in which the process is conducted in water, an organic solvent or a two-phase solvent system comprising water and a water-insoluble organic solvent.

18. A process according to claim 17 in which the organic solvent is in one or more of an alcohol; ketone; carboxylic acid; sulfone; sulfoxide; N,N-tetrasubstituted urea; N-alkylated lactam or N-dialkylated acid amide; ether; aliphatic, cycloaliphatic or aromatic hydrocarbon, which may be optionally substituted with F, Cl or $C_1$–$C_4$alkyl; carboxylic acid ester or lactone; a nitrile; or a glyme.

19. A process according to claim 1 in which the process is conducted in the presence of an organic base, an inorganic base or a mixture thereof which is added prior to step B).

20. A process according to claim 19 in which the base is used in an excess of up to 10 moles relative to the diazonium salt of formula (2) or (3).

21. A process according to claim 19 in which the base is a Li-, Na-, K-, $NH_4$-, Mg-, Ca- or $NH(C_1$–$C_{18}alkyl)_3$-salt of a carboxylic acid.

22. A process according to claim 21 in which the base is lithium-, potassium- or sodium acetate, -butyrate, -propionate or -stearate; barium- or calcium acetate; calcium propionate or -stearate; lithium- or sodium benzoate; ammonium acetate; or a salt of acetic acid with triethylamine, tri-n-butylamine, tri-(2-ethylhexylamine), tri-n-octylamine or tri-n-dodecylamine.

23. A process according to claim 22 in which the base is sodium or potassium acetate, or sodium or potassium bicarbonate, used in excess.

24. A process according to claim 1 in which the process is conducted at a temperature in the range of from −10 to 150° C.

25. A process according to claim 23 in which the process is conducted at a temperature in the range of from 0 to 120° C.

* * * * *